United States Patent
Ra (10) Patent No.: US 10,716,902 B2
(45) Date of Patent: Jul. 21, 2020

(54) FILTERING SYRINGE

(71) Applicant: Yong-Kuk Ra, Gumi-si (KR)

(72) Inventor: Yong-Kuk Ra, Gumi-si (KR)

( * ) Notice: Subject to any disclaimer, the term of this patent is extended or adjusted under 35 U.S.C. 154(b) by 129 days.

(21) Appl. No.: 16/086,727

(22) PCT Filed: Feb. 27, 2017

(86) PCT No.: PCT/KR2017/002112
§ 371 (c)(1),
(2) Date: Sep. 20, 2018

(87) PCT Pub. No.: WO2017/164528
PCT Pub. Date: Sep. 28, 2017

(65) Prior Publication Data
US 2019/0060575 A1    Feb. 28, 2019

(30) Foreign Application Priority Data

Mar. 22, 2016  (KR) .................. 10-2016-0034276

(51) Int. Cl.
*A61M 5/31* (2006.01)
*A61M 5/165* (2006.01)
(Continued)

(52) U.S. Cl.
CPC .......... *A61M 5/3145* (2013.01); *A61M 5/165* (2013.01); *A61M 5/162* (2013.01);
(Continued)

(58) Field of Classification Search
CPC ................ A61M 5/3145; A61M 5/165; A61M 2005/3128; A61M 5/162; A61M 5/343;
(Continued)

(56) References Cited

U.S. PATENT DOCUMENTS

| 4,180,071 A | 12/1979 | Oiwa |
| 2014/0213982 A1* | 7/2014 | Kim .................. A61M 5/3145 604/190 |
| 2016/0067410 A1 | 3/2016 | Carr et al. |

FOREIGN PATENT DOCUMENTS

| KR | 10-0902784 | 6/2009 |
| KR | 10-2009-0128108 | 12/2009 |

(Continued)

OTHER PUBLICATIONS

International Search Report for International Application No. PCT/KR2017/002112, dated Jun. 12, 2017.
(Continued)

*Primary Examiner* — Amber R Stiles
(74) *Attorney, Agent, or Firm* — LRK Patent Law Firm (57) ABSTRACT

The present invention relates to a filtering syringe, and more particularly, to an apparatus obtained by improving a syringe provided with a filter means for filtering foreign substances such as glass fragments of an ampoule, so that opening or closing of a one-way valve means is controlled depending on whether a cap is separated, and that the filter means can be also designed to be larger in cross-sectional area so as to allow a liquid medicine to be smoothly sucked with a smaller force. The filtering syringe is configured such that the liquid medicine is filtered and sucked through the filter means having the larger cross-sectional area even with the smaller force in a cap-assembled state and the one-way valve means is automatically closed to allow the liquid medicine to be injected in a cap-separated state, thereby maximizing user's convenience and marketability of the syringe.

3 Claims, 8 Drawing Sheets

(51) Int. Cl.
   *A61M 5/162* (2006.01)
   *A61M 5/32* (2006.01)
   *A61M 5/34* (2006.01)
(52) U.S. Cl.
   CPC .............. *A61M 5/32* (2013.01); *A61M 5/3202* (2013.01); *A61M 5/34* (2013.01); *A61M 5/343* (2013.01); *A61M 2005/3128* (2013.01)
(58) Field of Classification Search
   CPC .............. A61M 5/3202; A61M 5/1626; A61M 5/3293; A61M 5/34; A61M 5/32
   See application file for complete search history.

(56) References Cited

FOREIGN PATENT DOCUMENTS

| | | |
|---|---|---|
| KR | 10-2012-0087587 | 8/2012 |
| KR | 10-1335979 | 12/2013 |
| KR | 10-1600562 | 3/2016 |
| KR | 10-1680514 | 11/2016 |

OTHER PUBLICATIONS

English translation of the Written Opinion for International Application No. PCT/KR2017/002112, dated Jun. 12, 2017.

* cited by examiner

FIG. 1

Prior Art

FIG. 2

Prior Art

FIG. 3

Prior Art

FILTERING SYRINGE

TECHNICAL FIELD

The present invention relates to a filtering syringe, and more particularly, to an apparatus obtained by improving a syringe provided with a filter means for filtering foreign substances such as glass fragments of an ampoule, so that opening or closing of a one-way valve means is controlled depending on whether a cap is separated, and that the filter means can be also designed to be larger in cross-sectional area so as to allow a liquid medicine to be smoothly sucked with a smaller force, wherein the apparatus is configured such that the liquid medicine is filtered and sucked through the filter means having the larger cross-sectional area even with the smaller force in a cap-assembled state and the one-way valve means is automatically closed to allow the liquid medicine to be injected in a cap-separated state, thereby maximizing user's convenience and marketability of the syringe.

BACKGROUND ART

In general, a syringe is an instrument for injecting a liquid medicine into a body of an animal/plant and is configured to pierce a skin with a sharp tip thereof to allow the liquid medicine to be injected into any tissue of the body.

Figure 1:
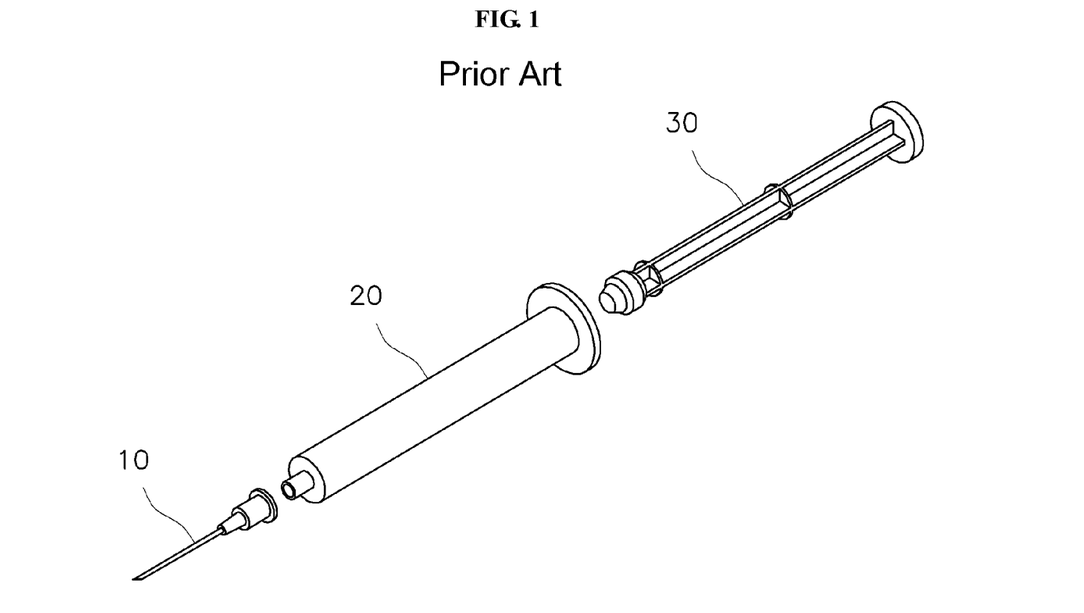
FIG. 1 is an exploded perspective view illustrating a conventional syringe.

FIG. 1 is an exploded perspective view illustrating a conventional syringe. As shown in FIG. 1, the syringe generally includes a cylinder 20 to which an injection needle 10 is coupled and in which an injection liquid is contained, and a plunger 30 provided in the cylinder 20 so as to be movable forward and backward.

In this conventional syringe, as the plunger 30 is moved backward, a negative pressure is generated in the cylinder 20 and the cylinder is then filled with an injection liquid. As the plunger is moved forward, the injection liquid in the cylinder 20 is discharged through the injection needle 10 by a positive pressure and then injected into a patient's body.

However, when this conventional syringe is used, there is concern that foreign substances incorporated in the injection liquid itself or foreign substances such as glass particles scattered into and mixed with the injection liquid during a process of breaking and opening an ampoule in which the injection liquid is stored may be injected together with the injection liquid into the patient's body.

To solve this problem, a filtering syringe provided with a filter for filtering foreign substances contained in an injection liquid has been developed.

First, as disclosed in Korean Patent Laid-Open Publication No. 2012-87587, a conventional filtering syringe in which a filter for filtering foreign substances is provided in an injection needle or a cylinder performs a function of filtering foreign substances from an injection liquid sucked into the cylinder.

However, since foreign substances had been stuck to an outer surface of the injection needle introduced into an ampoule when the injection liquid is sucked, or foreign substances incorporated in the injection liquid remaining within the injection needle had not been filtered, it was impossible to fundamentally prevent the foreign substances from being injected together with the injection liquid into a patient's body.

In response thereto, U.S. Pat. No. 4,180,071 discloses an example in which a filter for filtering foreign substances is provided in a cap for covering an injection needle.

Figure 2:
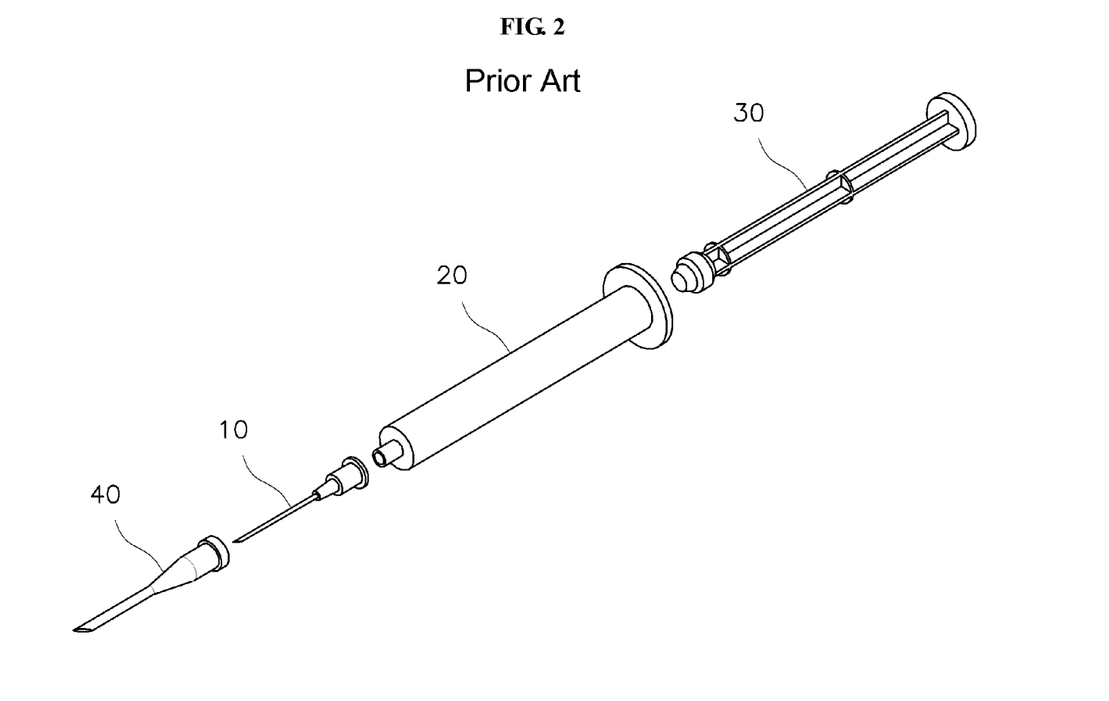
FIG. 2 is an exploded perspective view illustrating a conventional filter-cap syringe.
Figure 3:
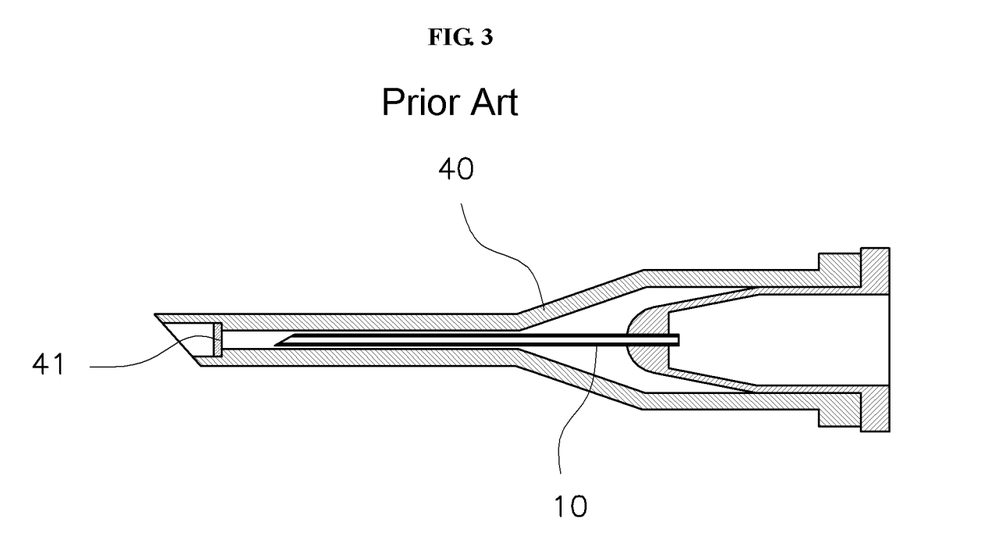
FIG. 3 is a sectional view illustrating a main portion of the conventional filter-cap syringe.

FIG. 2 is an exploded perspective view illustrating a conventional filter-cap syringe, and FIG. 3 is a sectional view illustrating a main portion of the conventional filter-cap syringe, wherein FIGS. 2 and 3 illustrate the conventional filter-cap syringe disclosed in U.S. Pat. No. 4,180,071.

Since the conventional filter-cap syringe has a cap 40 provided with a filter 41 as shown in FIG. 3 so that foreign substances are filtered by the filter 41 when an injection liquid is sucked, and the cap 40 including the filter 41 is detached from an injection needle 10 upon injection of the injection liquid, there is no concern that foreign substances may be injected.

However, in the conventional filter-cap syringe, the filter cap should have a diameter smaller than that of an inlet of a vial. If the diameter of the filter cap is larger, it is difficult to form a sharp tip having high strength and thus there is a limitation on increase in the area of the filter means.

In addition, the conventional filter-cap syringe has a technical problem in that since the injection liquid may be sucked into a cylinder 20 only via the minute injection needle 10 after passing through the filter 41 provided in the cap 40, a relatively large force is required for sucking the injection liquid and thus it is very inconvenient to use the syringe.

PRIOR ART DOCUMENT

Korean Patent Laid-Open Publication No. 2012-87587.
U.S. Pat. No. 4,180,071.

DISCLOSURE

Technical Problem

The present invention is conceived to solve these problems, and an object of the present invention is to provide a filtering syringe configured such that a liquid medicine is filtered and sucked through a filter means having a large cross-sectional area even with a smaller force in a cap-assembled state and a one-way valve means is automatically closed to allow the liquid medicine to be injected in a cap-separated state, thereby maximizing user's convenience and marketability of the syringe.

Technical Solution

According to the present invention, there is provided a filtering syringe including an injection needle comprised of a needle body and a hub, and a cylinder to which the injection needle is coupled, preferably, the hub of the injection needle is formed with an annular space having an inner wall surface, an outer wall surface and a bottom surface, and the bottom surface is formed with through-holes communicating with the cylinder; a one-way valve means made of an elastic material and having a cylindrical portion and a wing portion is provided on the inner wall surface, and an end of the wing portion is in elastic contact with the outer wall surface; a filter means is provided within the annular space between the one-way valve means and the though-holes; and the filtering syringe further includes a cap comprised of a hollow body with a sharp tip and hermetically coupled to an outer peripheral surface of the hub, wherein an opening/closing means surrounding the needle body is provided within the cap.

It is preferred that the one-way valve means is formed with a projection cooperating with an inner peripheral surface of the cap to promote deformation of the wing portion.

On the contrary, an inner peripheral surface of the cap may be formed with a protrusion cooperating with the one-way valve means to promote deformation of the wing portion.

Advantageous Effects

The filtering syringe of the present invention is configured such that a liquid medicine is filtered and sucked through a filter means having a large cross-sectional area even with a smaller force in a cap-assembled state and a one-way valve means is automatically closed to allow the liquid medicine to be injected in a cap-separated state, thereby maximizing user's convenience and marketability of the syringe.

BEST MODE

Figure 4:
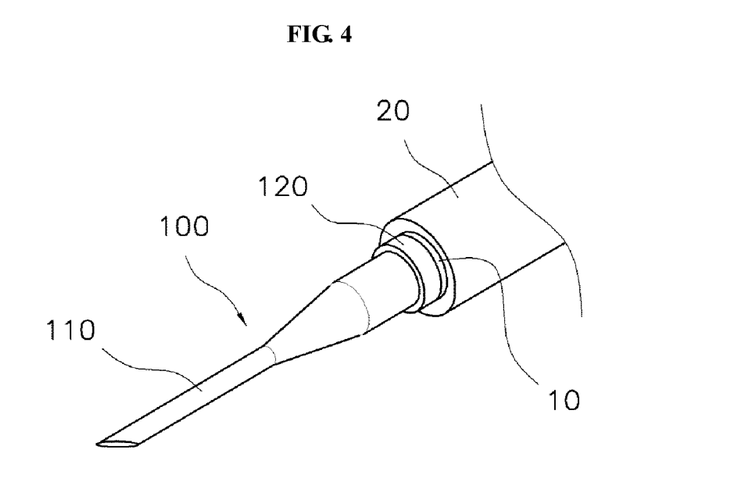
FIG. 4 is a perspective view illustrating a filtering syringe according to the present invention.
Figure 5:
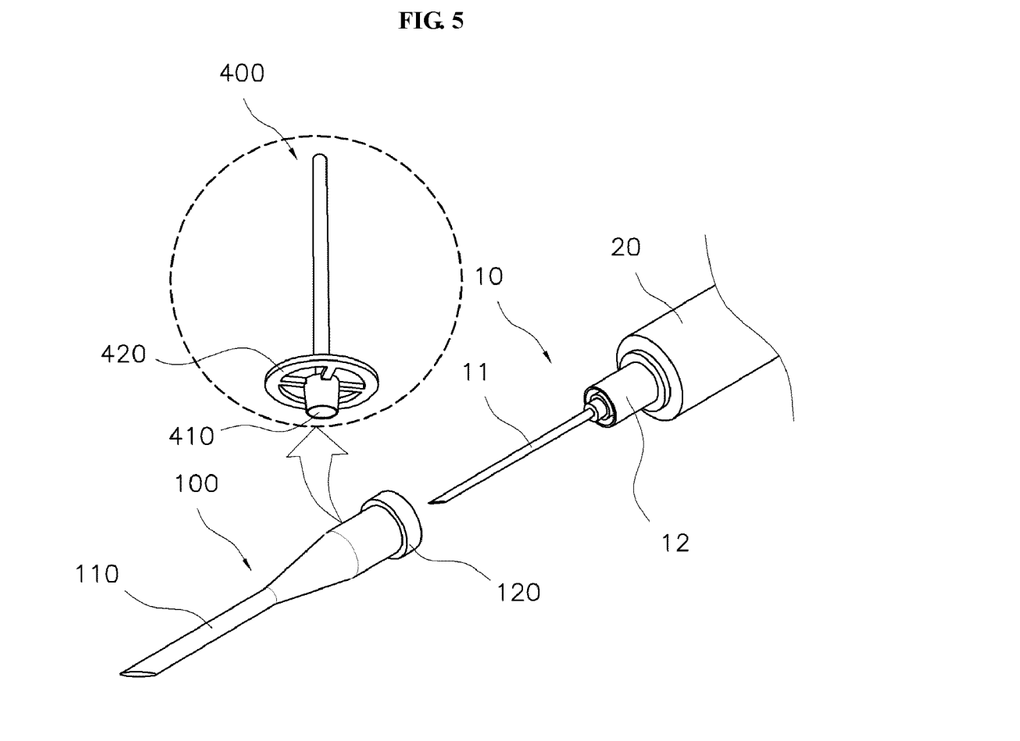
FIG. 5 is an exploded perspective view illustrating a state where a cap is separated in the filtering syringe according to the present invention.
Figure 6:
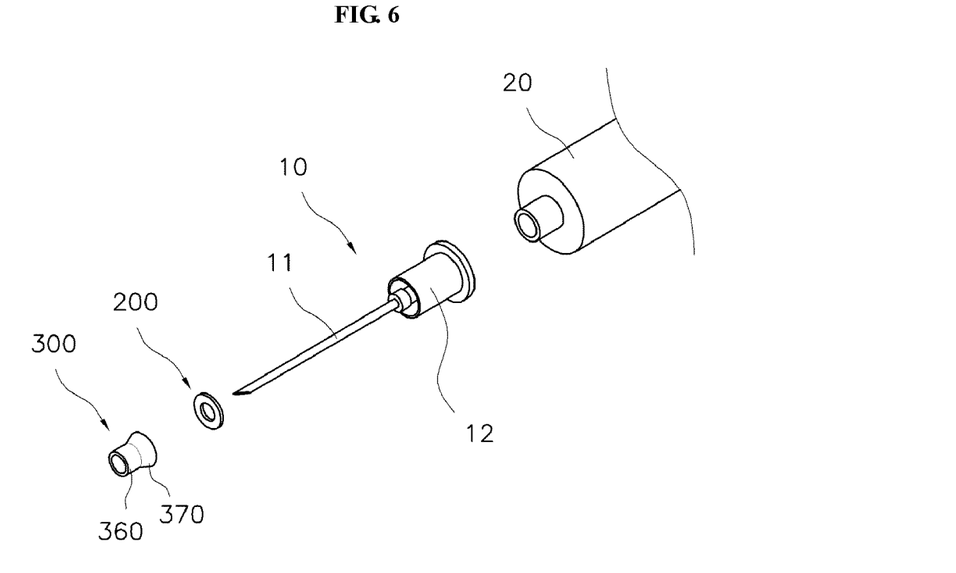
FIG. 6 is an exploded perspective view illustrating a state where an one-way valve means and a filter means are separated in the filtering syringe according to the present invention.

FIG. 4 is a perspective view illustrating a filtering syringe according to the present invention, FIG. 5 is an exploded perspective view illustrating a state where a cap is separated in the filtering syringe according to the present invention, and FIG. 6 is an exploded perspective view illustrating a state where an one-way valve means and a filter means are separated in the filtering syringe according to the present invention.

Figure 7:
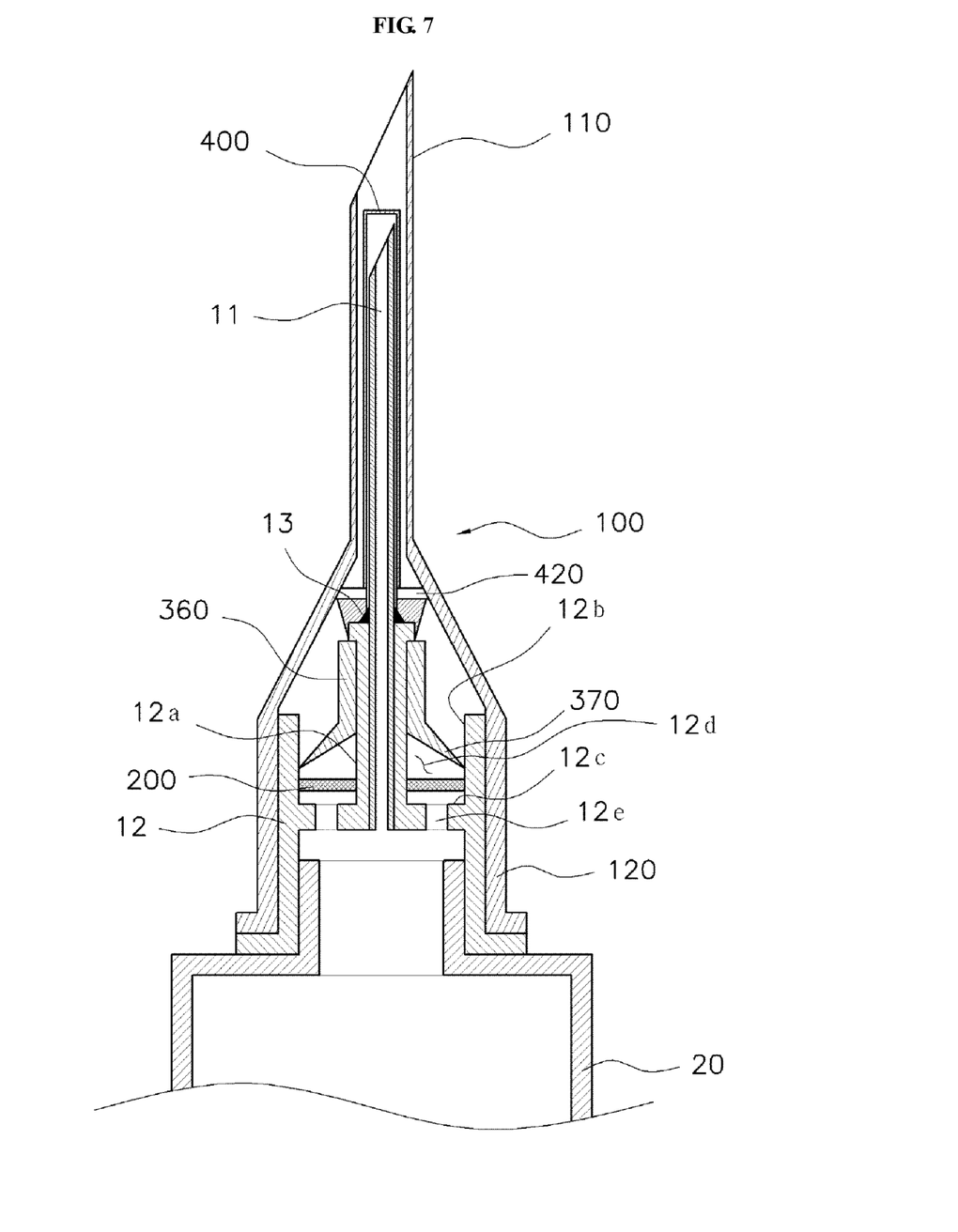
FIG. 7 is a sectional view illustrating the filtering syringe according to the present invention.
Figure 8:
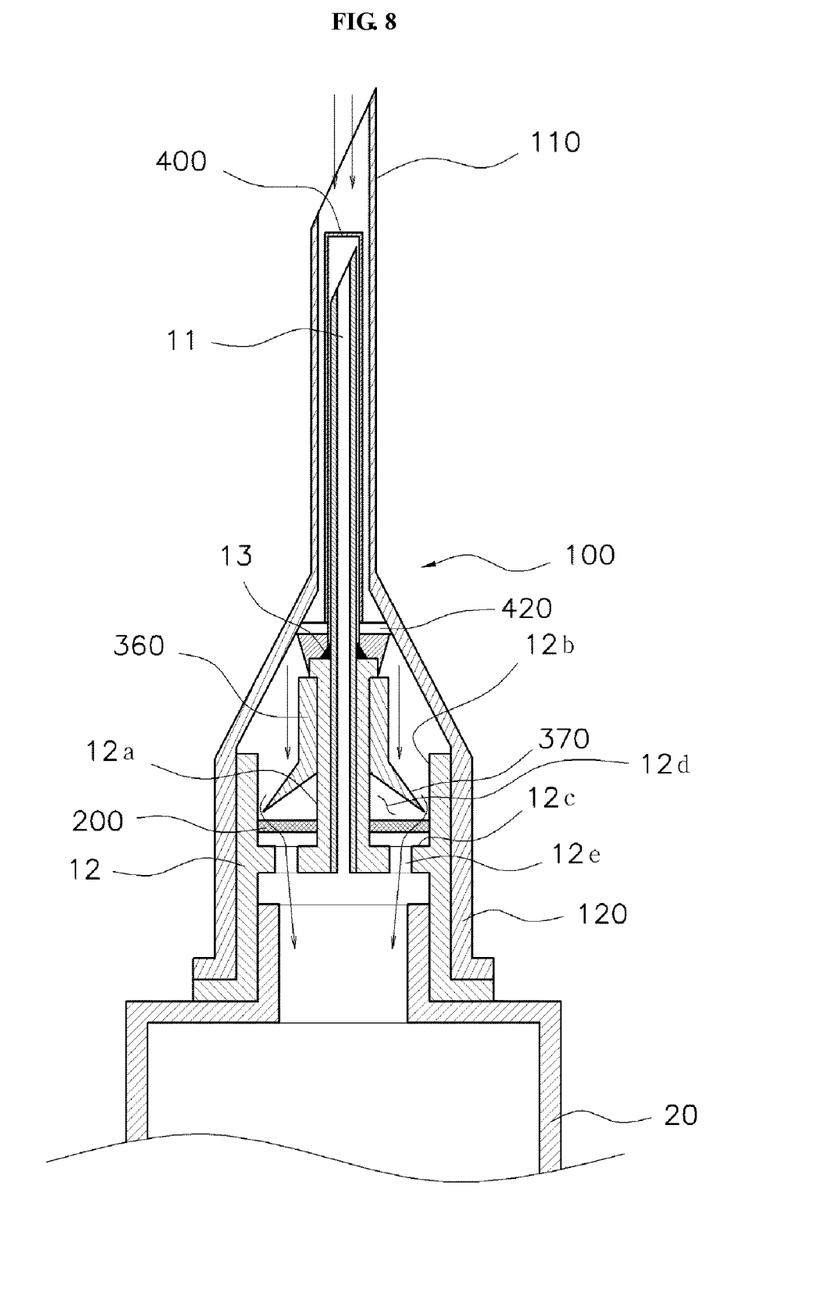
FIG. 8 is a sectional view illustrating a state where a liquid medicine is sucked in the filtering syringe according to the present invention.
Figure 9:
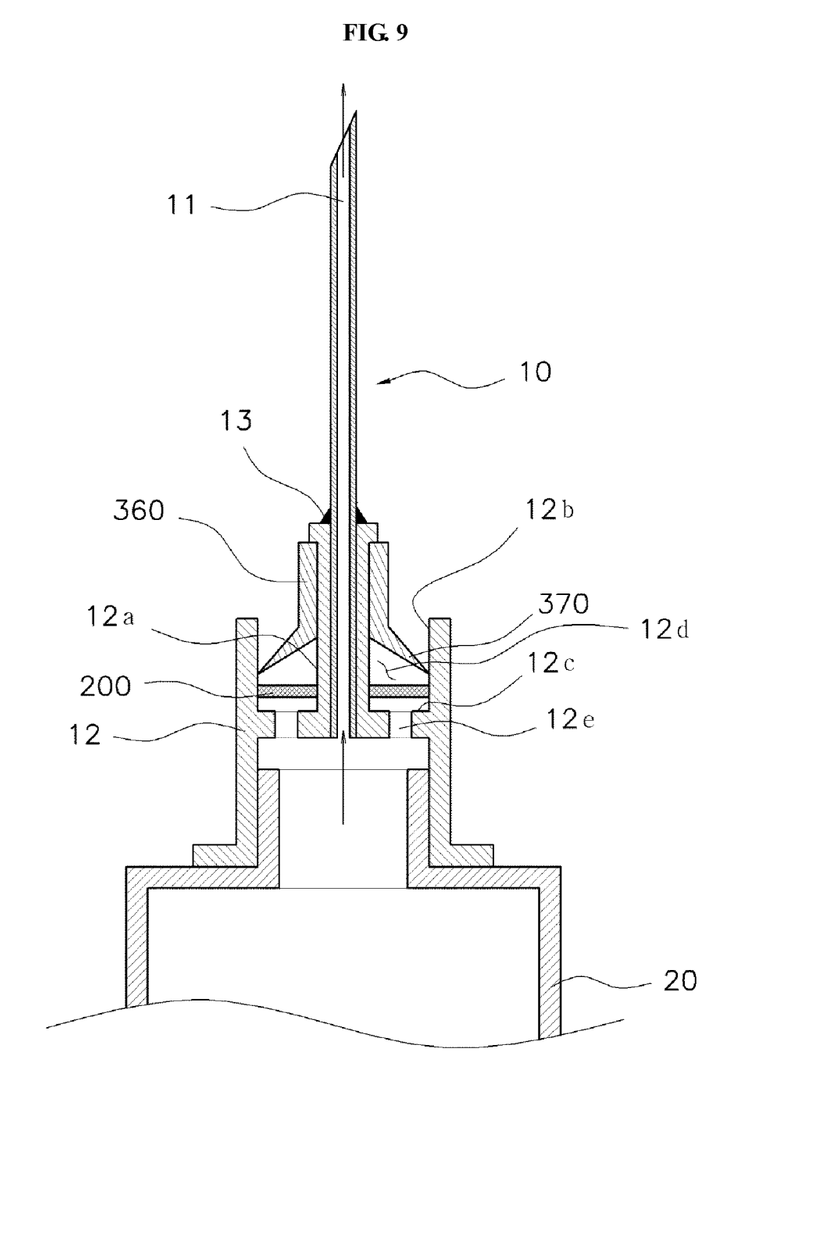
FIG. 9 is a sectional view illustrating a state where the liquid medicine is injected in the filtering syringe according to the present invention.

Moreover, FIG. 7 is a sectional view illustrating the filtering syringe according to the present invention, FIG. 8 is a sectional view illustrating a state where a liquid medicine is sucked in the filtering syringe according to the present invention, and FIG. 9 is a sectional view illustrating a state where the liquid medicine is injected in the filtering syringe according to the present invention.

Figure 10:
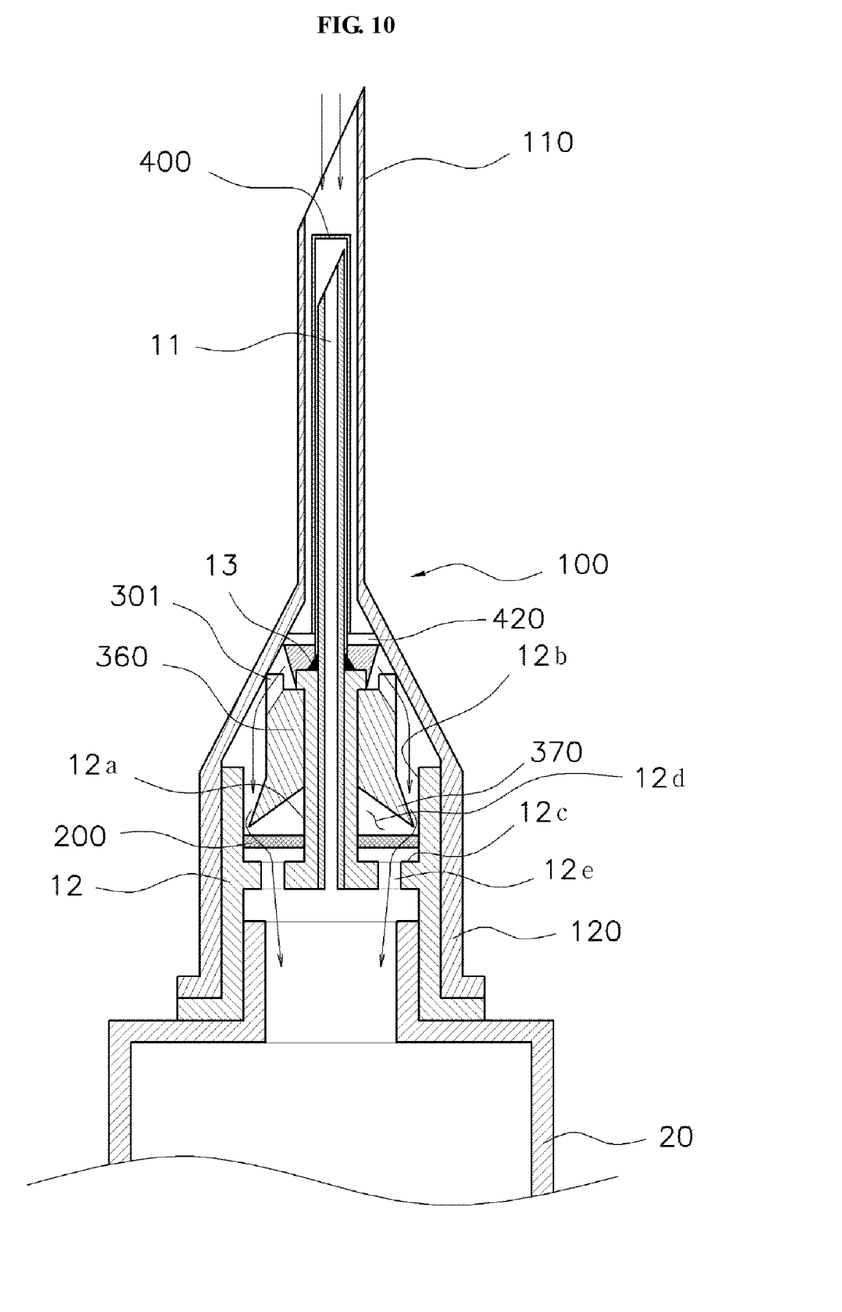
FIG. 10 is a sectional view illustrating another example of the one-way valve means of the filtering syringe according to the present invention.
Figure 11:
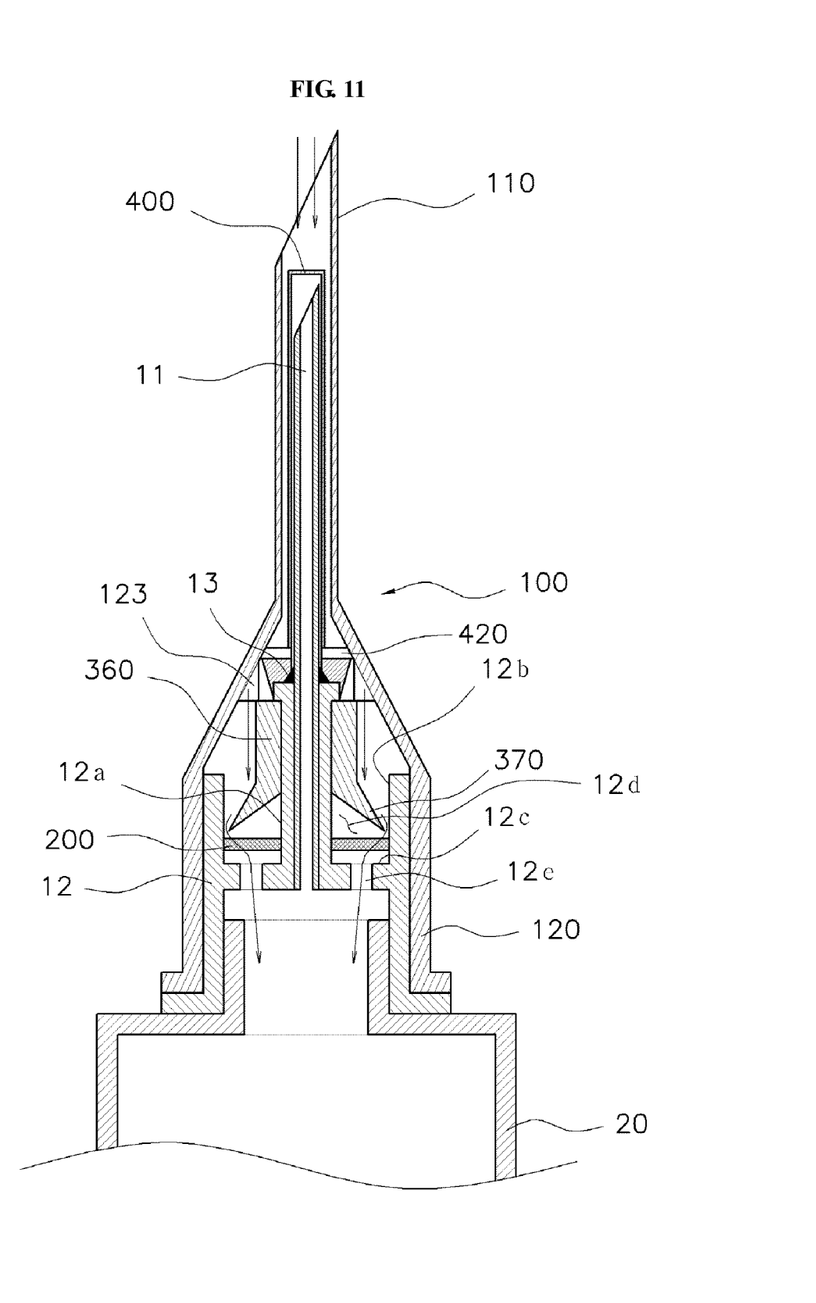
FIG. 11 is a sectional view illustrating another example of the cap of the filtering syringe according to the present invention.

In addition, FIG. 10 is a sectional view illustrating another example of the one-way valve means of the filtering syringe according to the present invention, and FIG. 11 is a sectional view illustrating another example of the cap of the filtering syringe according to the present invention.

As shown in FIGS. 4 to 11, the present invention relates to a filtering syringe which obtained by improving a syringe provided with a filter means for filtering foreign substances such as glass fragments of an ampoule, so that opening or closing of a one-way valve means 300 is controlled depending on whether a cap 100 is separated, and that the filter means 200 can be also designed to be larger in cross-sectional area so as to allow a liquid medicine to be smoothly sucked with a smaller force, wherein the filtering syringe is configured such that the liquid medicine is filtered and sucked through the filter means 200 having the larger cross-sectional area even with the smaller force in a cap-assembled state and the one-way valve means 300 is automatically closed to allow the liquid medicine to be injected in a cap-separated state, thereby maximizing user's convenience and marketability of the syringe.

Embodiments of the present invention will be described below in detail with reference to the accompanying drawings.

As shown in FIGS. 4 to 7, according to the present invention, there is provided a filtering syringe including an injection needle 10 comprised of a needle body 11 and a hub 12, and a cylinder 20 to which the injection needle 10 is coupled, preferably, the hub 12 of the injection needle 10 is formed with an annular space 12d having an inner wall surface 12a, an outer wall surface 12b and a bottom surface 12c, and the bottom surface 12c is formed with through-holes 12e communicating with the cylinder 20; a one-way valve means 300 made of an elastic material and having a cylindrical portion 360 and a wing portion 370 is provided on the inner wall surface 12a, and an end of the wing portion 370 is in elastic contact with the outer wall surface 12b; a filter means 200 is provided within the annular space 12d between the one-way valve means 300 and the though-holes 12e; and the filtering syringe further includes a cap 100 comprised of a hollow body with a sharp tip and hermetically coupled to an outer peripheral surface of the hub 12, wherein an opening/closing means 400 surrounding the needle body 11 is provided within the cap 100.

In the conventional syringe, a suction flow passage of the liquid medicine for allowing the liquid medicine to be sucked into the cylinder 20 was the same as an injection flow passage of the liquid medicine for allowing the liquid medicine to be injected through the injection needle 10.

However, with improvement of a well-known syringe including the injection needle 10, a cylinder 20 and a plunger, the filtering syringe of the present invention is provided with the suction flow passage from the liquid medicine-container to the cylinder 20, and the injection flow passage from the cylinder 20 to the injection needle 10, wherein the filter means 200 and a one-way valve means 300 are provided in the suction flow passage and a detachable opening/closing means 400 is provided in the injection flow passage. Preferably, a flow passage from the liquid medicine-container to the filter means 200 in the suction flow passage is formed independently of the outer peripheral surface of the injection needle 10 and the injection flow passage.

As such, the flow passage from the liquid medicine-container to the filter means 200 is a section in which a portion of the liquid medicine containing foreign substances such as glass fragments produced upon opening of the liquid medicine-container such as a glass ampoule may remain. By causing this section in which the foreign substances may remain to be formed independently of the outer peripheral surface of the injection needle 10 as well as the injection flow passage as described above, it is possible to fundamentally prevent foreign substances such as glass fragments from being injected into the body.

In other words, in the present invention, upon suction of the liquid medicine, the one-way valve means 300 in the suction flow passage is opened, so that the liquid medicine from which foreign substances are removed by the filter means 200 is sucked into the cylinder 20 of the syringe and the opening/closing means 400 closes the injection flow passage during the suction as shown in FIG. 8.

On the contrary, upon injection of the liquid medicine, the suction flow passage is closed by the one-way valve means 300, while the injection flow passage is opened by removing the opening/closing means 400 as shown in FIG. 9.

According to the embodiments, opening or closing of the one-way valve means 300 may be automatically adjusted depending on a direction of pressure on the liquid medicine, or may be adjusted depending on simply whether a cap 100 is separated.

In the present invention, the hub 12 constituting a part of the injection needle 10 is formed with an annular space 12d having an inner wall surface 12a, an outer wall surface 12b and a bottom surface 12c as shown in FIG. 7.

This annular space 12d is an empty space defined by rotating a generally U-shaped cross-section through 360 degrees about the needle body 11, wherein an outer peripheral surface surrounding the needle body 11 corresponds to the inner wall surface 12a, an inner peripheral surface of the hub 12 constitutes the outer wall surface 12b, and a horizontal surface connecting the inner wall surface 12a and the outer wall surface 12b constitutes the bottom surface 12c.

In this case, through-holes 12e are formed in the bottom surface 12c so that the liquid medicine may pass through the through-holes 12e and into the cylinder 20.

In particular, a one-way valve means 300 and a filter means 200 are placed within the annular space 12d.

The one-way valve means 300 is a component that is automatically opened or closed depending on a direction of pressure on the cylinder 20, is made of, for example, a flexible elastic material such as silicone and includes a cylindrical portion 360 and a wing portion 370 as shown in FIG. 6 and FIG. 7.

Here, the cylindrical portion 360 is configured to secure the one-way valve means 300, and surrounds and is coupled to the hub 12 of the injection needle 10. In this case, it is preferable that the hub 12 is formed with a stepped portion for preventing the one-way valve means 300 from being separated.

Moreover, an inclined lower end of the wing portion 370 is elastically contact with the outer wall surface 12b.

As a result, upon suction of the liquid medicine, an edge of the wing portion 370 is deformed downward as shown in FIG. 8 so that the one-way valve means 300 is opened, and upon injection of the liquid medicine, the edge of the wing portion 370 is brought into contact with the outer wall surface 12b of the annular space 12d as shown in FIG. 9 so that the one-way valve means 300 is closed.

Furthermore, the well-known filter means 200 capable of filtering foreign substances such as fine glass fragments is provided within the annular space 12d between the one-way valve means 300 and the through-holes 12e.

Accordingly, upon suction of the liquid medicine, the liquid medicine that has passed through the one-way valve means 300 is filtered by the filter means 200 to remove foreign substances and then flows into the cylinder 20 through the through-holes 12e of the annular space 12d.

In this case, the cap 100 is a component for sucking the liquid medicine from the liquid medicine-container, and includes the suction needle 110 and the cap hub 120. The sharp tip of the suction needle 110 is inclined to penetrate a vial or the like and is made of a metal material or a synthetic resin material so that it has a high strength.

Furthermore, the cap hub 120 is a component formed integrally with the suction needle 110 to support the suction needle 110, and the inner peripheral surface of the cap hub 120 is coupled to the outer peripheral surface of the hub 12, which supports the needle body 11 of the injection needle 10, to maintain airtightness.

In this case, the opening/closing means 400 surrounding the needle body 11 is provided within the cap 100 as shown in FIG. 5 and FIG. 7.

This opening/closing means 400 basically functions to open or close the needle body 11 as well as to prevent an exterior of the needle body 11 from being contaminated by the contaminated liquid medicine.

In other words, although the needle body 11 of the injection needle 10 was closed by the opening/closing means 400 upon suction of the liquid medicine, the opening/closing means 400 is separated to open the needle body 11 upon injection of the liquid medicine.

Particularly, in the present invention, it is possible to configure the opening/closing means 400 to include the hermetic space 410 and the flange 420 as shown in FIG. 5.

With this configuration, the opening/closing means 400 is fixedly installed the inner peripheral surface of the cap hub 120 of the cap 100 via the flange 420 so that the opening/closing means 400 may be integrally separated together with the cap 100.

In particular, in the present invention, it is preferable that the adhesive material 13 for incorporating the needle body 11 and the hub 12 of the injection needle 10 to each other is accommodated in the hermetic space 410 of the opening/closing means 400, which surrounds the injection needle 10 to maintain airtightness, so that the adhesive material is isolated from the liquid medicine.

Accordingly, it is possible to prevent degradation of an adhesive force of the adhesive material 13 due to contact of the adhesive material 13 with the liquid medicine, or alteration of components of the liquid medicine caused by the adhesive material 13.

With this configuration, the suction flow passage of the liquid medicine consists of the space between the cap 100 and the opening/closing means 400→the one-way valve means 300→the filter means 200→the through-holes 12e→the cylinder 20, and the injection flow passage of the liquid medicine consists of the cylinder 20→the injection needle 10.

As for the filtering syringe of the present invention described above, the opening or closing of the one-way valve means 300 depends on the direction of pressure on the cylinder 20, wherein when a negative pressure acts on the cylinder 20, the wing portion 370 of the one-way valve means 300 is spaced apart from the outer wall surface 12b as shown in FIG. 8, so that the liquid medicine introduced between the cap 100 and the opening/closing means 400 flows into the cylinder 20 through the opened one-way valve means 300, the filter means 200 and the through-holes 12e.

On the contrary, when a positive pressure acts on the cylinder 20 in a state where the cap 100 and the opening/closing means 400 are separated, the wing portion 370 of the one-way valve means 300 comes in contact with the outer wall surface 12b as shown in FIG. 9, so that the liquid medicine in the cylinder 20 does not pass through the closed one-way valve means 300 but is injected through the injection needle 10.

Although the one-way valve means 300 has been described above as being opened or closed depending on only the direction of pressure on the cylinder 20, there may be a structure for assisting in opening the one-way valve means 300 depending on whether the cap 100 is assembled.

To this end, it is preferable that, as shown in FIG. 10, a projection 301 cooperating with an inner peripheral surface of the cap 100 is formed on the one-way valve means 300 to promote deformation of the wing portion 370.

That is, the projection 301 is formed to protrude from an upper portion of the one-way valve means 300, and the projection is designed to have such a height that when the cap 100 is assembled, the projection comes in contact with the inner peripheral surface of the cap 100. As the cap 100 is assembled, the inner peripheral surface of the cap 100 comes in contact with the projection 301, whereby the wing portion 370 of the one-way valve means 300 may be deformed to induce the opening of one-way valve means 300.

In this case, a flow passage is defined with a certain gap at the projection 301 so as not to block a flow of the liquid medicine.

Of course, it is also possible to form the projection 301 to extend directly from the wing portion 370.

On the contrary, as shown in FIG. 11, a protrusion 123 cooperating with the one-way valve means 300 may be formed on the inner peripheral surface of the cap 100 to promote deformation of the wing portion 370.

In this case, the protrusion 123 is formed on the inner peripheral surface of the cap 100, and the protrusion preferably has such a height and location that it comes in contact with the one-way valve means 300 when the cap 100 is assembled.

With this configuration, the cylindrical portion 360 of the one-way valve means 300 is forced downward to induce downward deformation of the wing portion 370, so that the opening of the one-way valve means 300 may be promoted.

Even in this case, a flow passage is defined with a certain gap at the protrusion 123 so as not to block a flow of the liquid medicine.

In addition, it is also possible to form the protrusion 123 such that it extends to come in direct contact with the wing portion 370, whereby the wing portion 370 is forcibly spaced apart from the outer wall surface 12b by the protrusion 123.

Therefore, the filtering syringe of the present invention has great advantages in that the inlet of the suction flow passage and the outlet of the injection flow passage are completely separated from each other so that foreign substances such as glass fragments may be fundamentally prevented from being sucked together with the liquid medicine, and in that the one-way valve means 300 can be automatically opened or closed basically depending on the direction of pressure applied in the cylinder 20 and the opening or closing of the one-way valve means 300 can also be more smoothly performed by forming the separate projection 301 or protrusion 123.

In addition, there is a great advantage in that since the cross-sectional area of the filter means 200 can be increased to a desired area, it is possible for a user to easily suck and inject the liquid medicine with a smaller force even though the filter means 200 for filtering ultrafine foreign substances is employed.

Particularly, the liquid medicine can be sucked in the state where cap 100 has been assembled, and can also be injected only by separating the cap 100, thereby significantly enhancing user's convenience.

The aforementioned embodiments are merely examples for specifically explaining the spirit of the present invention, and the scope of the present invention is not limited to the figures and embodiments.

| [Explanation of Reference Numerals] | |
|---|---|
| 10: Injection needle | 11: Needle body |
| 12: Hub | 12a: Inner wall surface |
| 12b: Outer wall surface | 12c: Bottom surface |
| 12d: Annular space | 12e: Through-hole |
| 13: Adhesive material | 20: Cylinder |
| 30: Plunger | 100: Cap |
| 110: Suction needle | 120: Cap hub |
| 123: Protrusion | 200: Filter means |
| 300: One-way valve means | 301: Projection |
| 360: Cylindrical portion | 370: Wing portion |
| 400: Opening/closing means | 410: Hermetic space |
| 420: Flange | |

The invention claimed is:

1. A filtering syringe including an injection needle comprised of a needle body and a hub, and a cylinder to which the injection needle is coupled;
    wherein the hub of the injection needle is formed with an annular space having an inner wall surface, an outer wall surface and a bottom surface, and the bottom surface is formed with through-holes communicating with the cylinder;
    a one-way valve means made of an elastic material and having a cylindrical portion and a wing portion is provided on the inner wall surface, and an end of the wing portion is in elastic contact with the outer wall surface;
    a filter means is provided within the annular space between the one-way valve means and the through-holes; and
    the filtering syringe further comprises a cap comprised of a hollow body with a sharp tip and hermetically coupled to an outer peripheral surface of the hub, an opening/closing means surrounding a needle body of the injection needle being provided within the cap.

2. The filtering syringe of claim 1, wherein the one-way valve means is formed with a projection cooperating with an inner peripheral surface of the cap to promote deformation of the wing portion.

3. The filtering syringe of claim 1, wherein an inner peripheral surface of the cap is formed with a protrusion cooperating with the one-way valve means to promote deformation of the wing portion.

* * * * *